United States Patent
Lawson et al.

(10) Patent No.: US 6,802,863 B2
(45) Date of Patent: Oct. 12, 2004

(54) KEELED PROSTHETIC NUCLEUS

(75) Inventors: Kevin Jon Lawson, Redding, CA (US); Jens Peter Timm, Huntington Beach, CA (US)

(73) Assignee: Cross Medical Products, Inc., Irvine, CA (US)

( * ) Notice: Subject to any disclaimer, the term of this patent is extended or adjusted under 35 U.S.C. 154(b) by 49 days.

(21) Appl. No.: 10/374,190

(22) Filed: Feb. 26, 2003

(65) Prior Publication Data

US 2003/0176922 A1 Sep. 18, 2003

Related U.S. Application Data

(63) Continuation-in-part of application No. 10/097,711, filed on Mar. 13, 2002.

(51) Int. Cl.⁷ .................................................. A61F 2/44
(52) U.S. Cl. .................................. 623/17.16; 623/17.11
(58) Field of Search ........................... 623/17.11–17.16, 623/20.18

(56) References Cited

U.S. PATENT DOCUMENTS

| | | | | | |
|---|---|---|---|---|---|
| 4,205,400 A | * | 6/1980 | Shen et al. | ............... | 623/17.11 |
| 5,080,674 A | * | 1/1992 | Jacobs et al. | ............. | 623/20.17 |
| 5,197,986 A | * | 3/1993 | Mikhail | ................... | 623/20.18 |
| 5,861,041 A | * | 1/1999 | Tienboon | ................. | 623/17.16 |
| 6,146,422 A | * | 11/2000 | Lawson | ................... | 623/17.16 |
| 6,315,798 B1 | * | 11/2001 | Ashby et al. | ............. | 623/20.17 |

* cited by examiner

*Primary Examiner*—Pedro Philogene
*Assistant Examiner*—David A Bonderer
(74) *Attorney, Agent, or Firm*—Robert Charles Hill

(57) ABSTRACT

A prosthetic nucleus replacement embodiment of the present invention comprises a rounded shaped ceramic domed body with a receptacle in its bottom side. A keeled base of biocompatible metal is press-fit into the receptacle at any relative angle to complete a two-piece assembly. A keel part of the base especially is finished in porous coated metal and shaped to promote natural in-growth of bone from the inferior vertebrae.

5 Claims, 2 Drawing Sheets

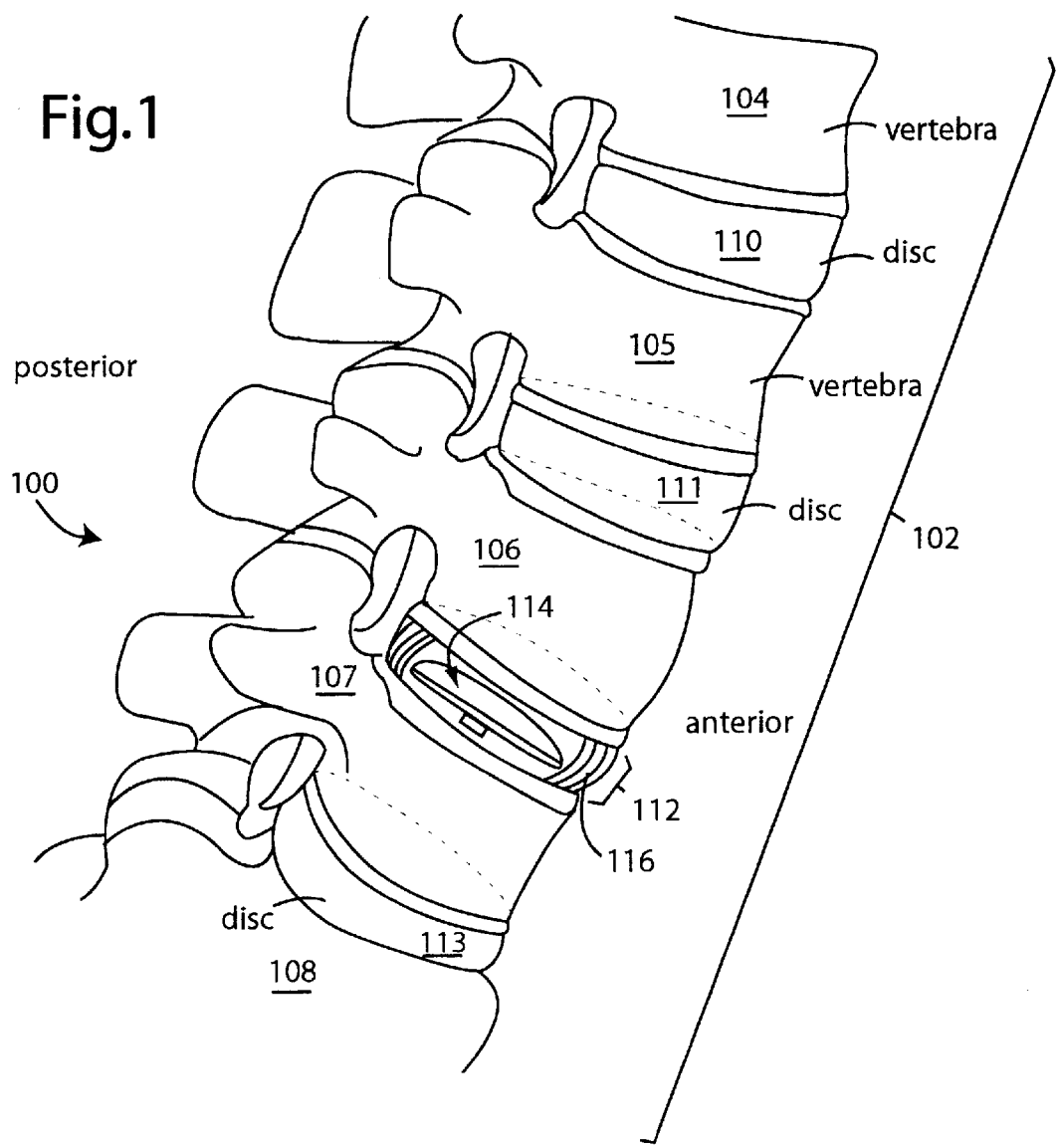

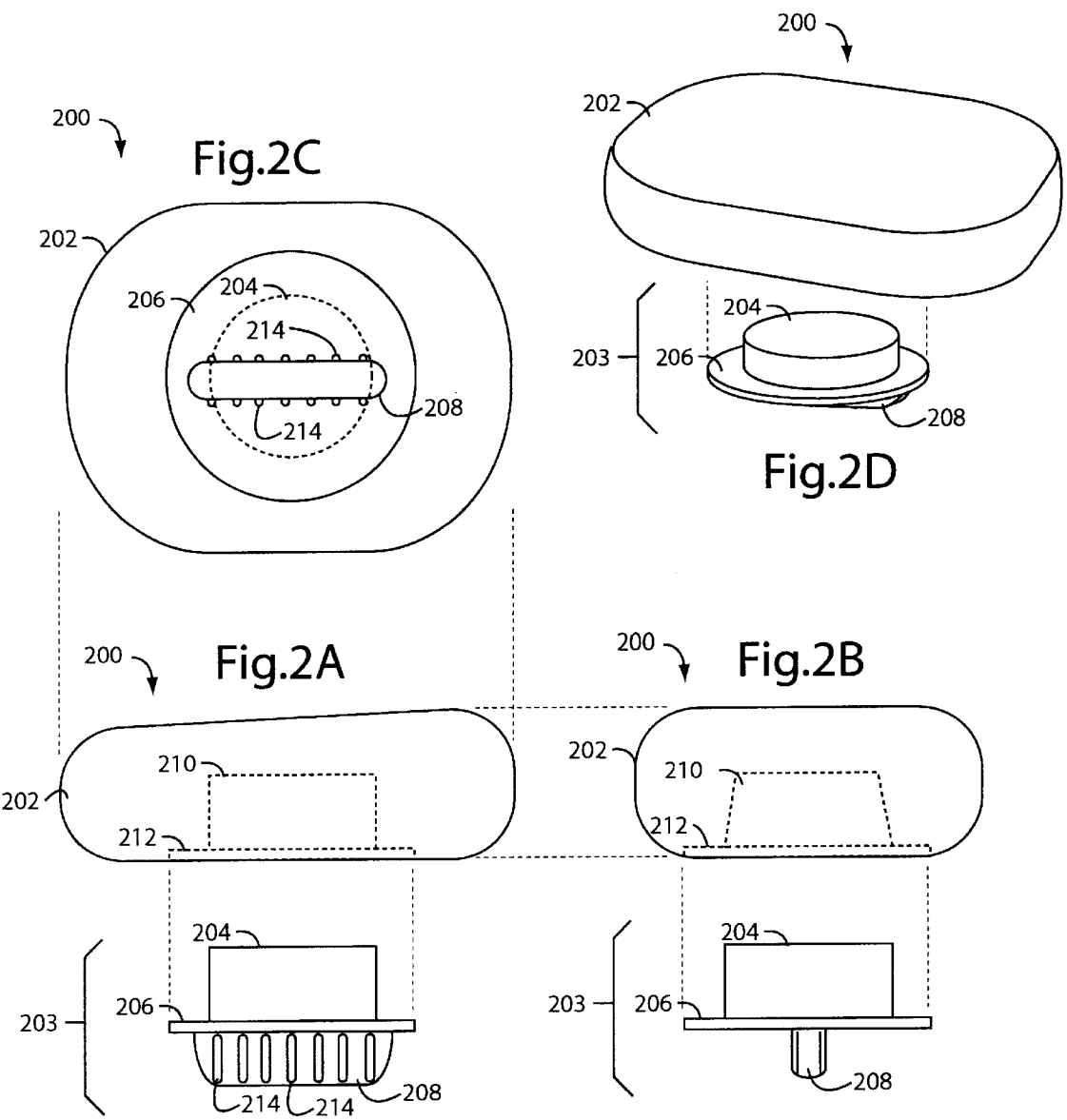

KEELED PROSTHETIC NUCLEUS

COPENDING APPLICATION

This Application is a continuation-in-part of U.S. patent application, Ser. No. 10/097,711, filed Mar. 13, 2002, and titled, TWO-PART PROSTHETIC NUCLEUS REPLACEMENT FOR SURGICAL RECONSTRUCTION OF INTERVERTEBRAL DISCS. Such Application is incorporated herein by reference.

BACKGROUND OF THE INVENTION

1. Field of the Invention

The present invention relates to surgical methods and devices to treat back and leg pain, and in particular to two-part prosthetic nucleus replacements for surgical insertion within the annulus fibrosis. Such prosthesis replaces a portion of a damaged spinal intervertebral disc to restore function.

2. Description of Related Art

The principal function of the disco-vertebral joint in the human spine is to transmit compressive loads and still allow flexibility. Adjacent vertebrae are joined by a triple-joint complex. The anterior complex, or column, is formed by the vertebral bodies which are shaped like flattened cylinders with discoid and ovoid shaped intervertebral discs sandwiched between each vertebral body. Facet joints in the rear of each vertebra have a smooth cartilage surface, lubricating joint fluid, and a covering capsule. The facet joints restrict the disc to small degrees of flexion and extension, limit rotation, and protect against translational shear stress. The disc itself comprises two principle parts, the nucleus pulposus at the core, and the annulus fibrosis, which is a multi-layer bias-ply wrapping that surrounds the nucleus. The nucleus starts early in life as eighty percent water, and slowly desiccates with age or as a result of injury.

A damaged disc can cause nerve dysfunction and debilitating pain in the back, legs and arms. Typical treatments that provide relief and allow patients to function again include back braces, medical treatment, physical therapy and surgery to remove the disc. A conventional surgical solution removes the bad disc and promotes new bone growth in the space to fuse the adjacent vertebrae together.

Several different prosthetic intervertebral disc devices are described by Casey K. Lee, et al., in "Prosthetic Intervertebral Disc," Chapter 96, *The Adult Spine: Principles and Practice*, Raven Press, Ltd., New York, © 1991. The conclusion of Lee, et al., is that "An appropriately designed and fabricated prosthetic intervertebral disc may provide an improved alternative to currently available surgical approaches to low back disorders." Lee, et al., describe their work at the orthopedic research laboratories at the New Jersey Medical School "to produce a prosthetic interverte-bral disc design that has biomechanical characteristics similar to the natural disc." One result has been the manufacture of a unit with a nucleus, annulus, and end plates that are molded under heat and fused into a single prosthetic disc. However, success of such a device depends on solid bone attachment. Most prior concepts have been excessively complex and never used.

A prosthetic nucleus replacement can be surgically implanted within the annulus fibrosis. The natural attachments of the annulus would therefore be able to produce the requisite tensile strength of the repaired site. The prosthetic nucleus replacement would be subject primarily to compressive forces.

Such a prosthetic nucleus replacement is described by the present inventor, Kevin Lawson, in U.S. Pat. No. 6,146,422, issued Nov. 14, 2000. But this device is composed of one homogeneous material and thus its top and bottom sides exhibit identical material characteristics. The described construction can also be unnecessarily expensive to produce and difficult to fabricate.

SUMMARY OF THE INVENTION

An object of the present invention is to provide a prosthetic nucleus replacement that is useful and functional.

Another object of the present invention is to provide a prosthetic nucleus replacement that allows for bone in-growth on the inferior surface.

A further object of the present invention is to provide a prosthetic nucleus replacement that allows for a press-fit interface with the inferior vertebral bone.

Briefly, a prosthetic nucleus replacement embodiment of the present invention comprises a rounded ceramic domed body with a receptacle in its bottom side. A keeled base of titanium or other biocompatible metal is press fit into the receptacle to complete a two-piece assembly. A keel part of the base especially is finished in porous coated metal and shaped to promote natural in-growth of bone from the inferior vertebrae.

An advantage of the present invention is that a prosthetic nucleus replacement is provided that supports the normal compressive loads experienced by natural vertebrae.

Another advantage of the present invention is that a prosthetic nucleus replacement is provided that fixes well to the inferior vertebrae it sits upon.

A further advantage of the present invention is that a prosthetic nucleus replacement is provided that slides easily under the superior vertebrae it supports.

A still further advantage of the present invention is that a prosthetic nucleus replacement is provided that has optimal top and bottom characteristics by virtue of its joining of two dissimilar top and bottom materials.

A further advantage of the present invention is that a prosthetic nucleus replacement is provided that has a two-piece construction which allows for a wide variety of implant alignments.

The above and still further objects, features, and advantages of the present invention will become apparent upon consideration of the following detailed description of specific embodiments thereof, especially when taken in conjunction with the accompanying drawings.

BRIEF DESCRIPTION OF THE DRAWINGS

FIG. 1 is a diagram representing the spine of a patient with a prosthetic nucleus replacement embodiment of the present invention;

FIG. 2A is a lateral, side view a two-part prosthetic nucleus replacement embodiment of the present invention similar to that shown in FIG. 1;

FIG. 2B is a posterior-anterior, end view of the two-part prosthetic nucleus replacement embodiment of the present invention shown in FIG. 2A;

FIG. 2C is an inferior, bottom view of the two-part prosthetic nucleus replacement embodiment of the present invention shown in FIGS. 2A–2B; and FIG. 2D is a perspective, exploded assembly view of the two-part prosthetic nucleus replacement embodiment of the present invention shown in FIGS. 2A–2C.

DETAILED DESCRIPTION OF THE INVENTION

FIG. 1 illustrates a prosthetic spinal nucleus replacement embodiment of the present invention, referred to herein by the general reference numeral 100. A human spine 102 commonly comprises a series of vertebrae 104–108 interdigitated with a corresponding series of discs 110–113. Each natural disc comprises a nucleus pulposus surrounded and contained by a corresponding annulus fibrosis. Natural nucleus pulposus have jelly-like structures that can resist compressive loads. Natural annulus fibrosis structures comprise multiple layers of bias-ply filaments set at forty-degree angles that resemble the construction of an automobile bias-ply tire carcass.

Disc 112, between vertebra 106 and 107, is assumed in FIG. 1 to be degenerated. The spinal nucleus replacement prosthesis 114 is surgically embedded in the inter-vertebral space between vertebra 106 and 107, and inside an annulus fibrosis 116.

Prosthetic nucleus replacement embodiments of the present invention comprise a two-part modular assembly that resembles a flattened oval disk. The superior, or top part is domed and is made of a biocompatible material that slides easily and articulates well with the superior vertebrae 106. The inferior base part is made of a different biocompatible material that can be fixed readily to the bone of the inferior vertebrae 107. For example, a porous material for bone in-growth, or a textured material for cementing. The possible biocompatible materials include ceramics, polymers and plastics, titanium, stainless steel, tantalum, chrome cobalt alloys, etc. A ceramic material is preferred in the nucleus replacement prosthesis 114.

In general, prosthetic nuclei of the present invention are implanted using a straight anterior or anterior lateral approach with incision of the anterior longitudinal ligaments of the annulus. Just before use, and after the implant site has been evaluated, a prosthetic annulus is assembled from two modular parts at the appropriate angles for the particular application. E.g., a top dome and a base made of dissimilar materials. A flap technique is used for the incision of the annulus, and such tissues are closed back up with conventional sutures or suture anchors to the bone. The endplate cartilage of the superior vertebrae is preserved for permanent articulation with the implanted nucleus prosthetic. The endplate cartilage of the inferior vertebrae is curetted down to bone. The bone is prepared to receive a keel protruding below from the implanted nucleus prosthetic. Such keel and its porous coated metal construction help to permanently immobilize this interface. The whole assembly is carefully centered within the intervertebral space as far posterior as possible to help reestablish natural kinematics of flex-extension, lateral bending, and intervertebral height. The keel and/or its base allow a variety of relative alignments with the domed body to suit particular angles of surgical approach.

FIGS. 2A–2D represent a prosthetic nucleus replacement embodiment of the present invention, and such is referred to herein by the general reference numeral 200. The prosthetic nucleus replacement 200 comprises a domed body 202 having a rounded smooth appearance and shape. The complex convex top surface is polished and intended to slide easily when in contact with the cartilage of a superior vertebrae. A second part is a base 203 made of porous coated metal and having a press-fit plug 204, a lip 206, and a keel 208. The plug 204 and lip 206 fit tightly into a receptacle 210 and ring groove 212 in the bottom of the domed body 202. The porous coated metal construction of the keel, e.g., titanium or other biocompatible metal, promotes and accepts bone in-growth from the inferior vertebrae. Such may be augmented by a series of ribs 214 disposed on the sides of the keel 208.

A surgical method embodiment of the present invention for correcting a degenerated nucleus pulposus by the implantation of a prosthetic in a human spine begins with a flap-technique incision of an annulus fibrosis corresponding to an affected area of a spine. Then a diskectomy of a degenerated nucleus pulposus is done in the affected area. The cartilage is cut down to the bone of an inferior vertebrae adjacent to the affected area and the bone is prepared for anchoring to a modular annulus base. A nucleus is then assembled from interlocking ones of a domed body of a ceramic material and a base with a keel made of porous coated metal. The two-part assembly provides for replacement of a natural nucleus pulposus. The assembly is inserted into the affected area through an incision in the annulus fibrosis. The replacement is immobilized with respect to the inferior vertebrae, e.g., first by the shape of the keel and more permanently by bone in-growth. And, then the incision in the annulus fibrosis is closed. The result is a permanent articulation between the solid ellipsoidal body and a superior vertebrae after surgery and recovery.

The present inventor's previous U.S. Pat. No. 6,146,422, issued Nov. 14, 2000, is incorporated herein by reference.

The replacement nucleus top must be biocompatible, exhibit a low coefficient of friction, have a smooth surface, be resilient, and if possible radiolucent. It should help produce clear easy to read x-ray, CAT, and/or MRI medical images, e.g., to enable post-operative evaluations that are non-invasive.

The bottom of the replacement nucleus must also be biocompatible, but it should stay immobile and thus have a high coefficient of friction. Bone in-growth from below is desirable.

Although particular embodiments of the present invention have been described and illustrated, such was not intended to limit the invention. Modifications and changes will no doubt become apparent to those skilled in the art, and it was intended that the invention only be limited by the scope of the appended claims.

What is claimed is:

1. A prosthetic nucleus replacement for implanting within an annulus fibrosis in one part of a human spine, comprising:

a domed body comprised of ceramic material formed into a rounded shape, and having a complex convex upper side for contacting and articulating with an end-plate cartilage of a supported superior vertebrae;

a receptacle disposed in an inferior surface of the domed body;

a base having a top surface that matches the receptacle and provides for mechanical attachment to the domed body, and comprised substantially of a biocompatible porous coated metal material;

a keel disposed in the base and protruding from a bottom surface and providing for an immobile foundation on an underlying inferior vertebrae;

wherein, a top surface of the domed body slides easily when in contact with said supported superior vertebrae; and wherein, the keel and said porous coated metal material provide a firm mechanical interface and make possible bone in-growth from said inferior vertebrae and permanent anchoring.

2. The prosthetic nucleus replacement of claim 1, further comprising:

a plurality of ribbing on the keel for promoting bone in-growth from said inferior vertebrae and permanent anchoring.

3. The prosthetic nucleus replacement of claim 1, wherein:

the receptacle is such that a plurality of bases can be modularly adapted in different combinations with the domed body, and the base material includes a biocompatible metal.

4. The prosthetic nucleus replacement of claim 1, wherein:

the keel and domed body allow a variety of relative alignments to suit particular angles of surgical approach.

5. A method for surgically correcting a degenerated nucleus pulposus by the implantation of a prosthetic in a human spine, the method comprising:

a flap technique incision of an annulus fibrosis corresponding to an affected area of a spine;

a diskectomy of a degenerated nucleus pulposus in said affected area;

curetting of cartilage down to the bone of an inferior vertebrae adjacent to said affected area and preparing said bone to receive a pin;

selecting a domed body with a receptacle disposed in an inferior surface, and comprising ceramic material formed into a rounded shape, and having a complex convex upper side for contacting and articulating with an end-plate cartilage of a supported superior vertebrae;

assembling the domed body to a base having a top surface that matches said receptacle and that provides for mechanical attachment to the domed body, and which is comprised substantially of a biocompatible porous coated metal material, and further comprises a keel disposed in said base which protrudes from a bottom surface and provides for an immobile foundation on an underlying inferior vertebrae;

inserting said solid ellipsoidal body into said affected area through an incision in said annulus fibrosis;

immobilizing said solid ellipsoidal body with respect to said inferior vertebrae; and repairing incision in said annulus fibrosis;

wherein, bone in-growth is promoted from said underlying inferior vertebrae into said keel; and wherein, a permanent articulation between said solid ellipsoidal body and a superior vertebrae exists after surgery.

* * * * *